United States Patent [19]

Shibamoto et al.

[11] Patent Number: 4,853,407

[45] Date of Patent: Aug. 1, 1989

[54] AMINOETHYLCYSTEINE DERIVATIVES

[75] Inventors: Norio Shibamoto, Chigasaki; Takeo Yoshioka, Ayase; Yasuo Fukagawa, Kamakura; Tomoyuki Ishikura, Chigasaki, all of Japan

[73] Assignee: Sanraku Incorporated, Tokyo, Japan

[21] Appl. No.: 197,446

[22] Filed: May 20, 1988

[30] Foreign Application Priority Data

May 22, 1987 [JP] Japan .................. 62-124055

[51] Int. Cl.⁴ .................. A61K 31/40; C07D 209/48
[52] U.S. Cl. .................. 514/414; 514/417; 514/562; 548/462; 548/477; 562/426
[58] Field of Search .......... 562/426; 548/462, 477; 514/414, 417, 562

[56] References Cited

U.S. PATENT DOCUMENTS 4,528,397  7/1985  Shibamoto et al. .......... 514/400

FOREIGN PATENT DOCUMENTS

| 51023 | 4/1980 | Japan . |
| 81518 | 7/1981 | Japan . |
| 170479 | 10/1983 | Japan . |
| 93117 | 5/1986 | Japan . |
| 54322 | 3/1988 | Japan . |

Primary Examiner—Mary E. Ceperley
Attorney, Agent, or Firm—Wenderoth, Lind & Ponack

[57] ABSTRACT

Compounds represented by formula $$Y^1-CH_2-CH_2-S-CH_2-\underset{\underset{Y^2}{|}}{CH}-COOH \qquad (I)$$

wherein $Y^1$ and $Y^2$ are identical or different, and respectively denote benzoylamino groups or phthalimide groups. This compound is useful for inhibition of dipeptidase.

5 Claims, No Drawings

AMINOETHYLCYSTEINE DERIVATIVES

This invention relates to novel aminoethylcysteine derivatives, and more specifically, it relates to compounds having dipeptidase-inhibiting activity and represented by formula $$Y^1-CH_2-CH_2-S-CH_2-\underset{Y^2}{CH}-COOH \quad (I)$$

wherein $Y^1$ and $Y^2$ are identical or different and respectively denote benzoylamino groups or phthalimide groups.

In recent years, a group of carbapenem-type antibiotics having a basic skeleton represented by the following formula

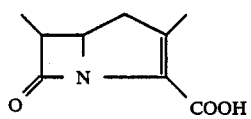

has been found and attracts attention as antibiotics of next generation having broad antibacterial spectra against gram-negative, gram-positive and beta-lactamase-producing bacteria.

It is generally thought that in the mechanism of expression of antibacterial action of these carbapenemtype antibiotics, synthesis of cell walls of bacteria is inhibited as in the beta-lactam-type antibiotics such as penicillin-type antibiotics, cephalosporin-type antibiotics, and the like. Therefore, there is an urgent need for development of the carbapenem-type antibiotics as useful antibiotics having little toxicity to mammals having no cell walls.

However, as is reported by Kropp, H. et al., Abstract No. 272, 20th Intersci. Conf. Antimicr. Agents & Chemoth., New Orleans (1980), it is known that these carbapenem-type antibiotics have a crucial defect that they are converted to inactive substances due to metabolism in living animals, particularly in the kidney. And the mechanism in this metabolism is believed to be hydrolysis of a beta-lactam ring by particulate renal dipeptidase.

Accordingly, several substances which have enzyme-inhibiting activity against dipeptidase have been found in order to inhibit metabolism of the carbapenem-type antibiotics to improve the concentration of said antibiotics in the blood and the half life thereof in the blood by using said enzyme inhibitors in combination with the carbapenem-type antibiotics, and these enzyme inhibitors are proposed [e.g., in Japanese Patent Publication No. 60816/1986].

The present inventors have already found and proposed an antibotic PS-5 (Okamura et al., J. Antibiotics, vol. 32, pages 262–271, 1979), antibiotic PS-6 and antibiotic PS-7 (Shibamoto et al., J. Antibiotics, vol. 33, pages 1128–1137, 1980) as carbapenem-type antibiotics. The present inventors have also diligently made researches on dipeptidase inhibitors which work to prevent the metabolism of the carbapenem-type antibiotics. As a result, they have found that the aminoethylcysteine derivatives of the aforementioned formula (I) have strong dipeptidase-inhibiting activity, and this finding has led to completion of this invention.

In the compounds of the aforementioned formula (I) provided by this invention, $Y^1$ and $Y^2$ may be identical or different. Hence, included in the formula (I) are the following four compounds.

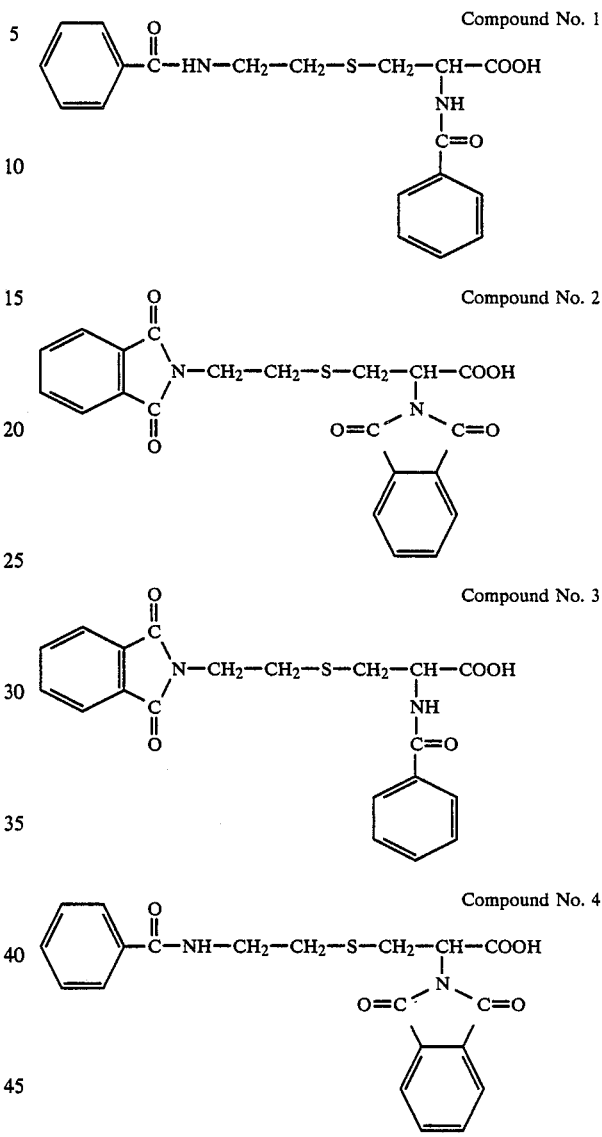

The compounds of formula (I) provided by this invention can be prepared, for example, by the following processes.

(a) In the case where $Y^1$ and $Y^2$ are identical:

An aminoethylcysteine represented by the following formula (II)

$$H_2N-CH_2-CH_2-S-CH_2-\underset{NH_2}{CH}-COOH \quad (II)$$

is allowed to react with two or more equivalents of a reactive derivative of benzoic acid or phthalic acid under the amidation reaction conditions known per se.

(b) In the case where $Y^1$ and $Y^2$ are different from each other:

(b-1) An aminoethylcysteine of the above formula (II) is allowed to react with a nearly equimolar amount of a reactive derivative of one acid of benzoic acid and phathalic acid under the acylation reaction conditions known per se to obtain a compound represented by the following formula

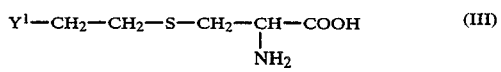

wherein $Y^1$ is as defined hereinabove. then, the compound of formula (III) is allowed to react with a nearly equimolar amount or more of a reactive derivative of the other acid of the above two acids under the amidation reaction conditions known per se, or (b-2) a compound represented by formula

wherein Hal denotes a halogen atom such as a chlorine or bromine atom and $Y^1$ is as defined above, (e.g., N-chloroethylbenzamide, N-bromoethylbenzamide, N-chloroethylphthalimide, N-bromoethylphthalimide, etc.) is allowed to react with a compound represented by formula

wherein $Y^2$ is as defined above.

Examples of the above reactive derivatives of benzoic acid or phthalic acid used in amidation reaction include halides such as benzoic acid chloride, benzoic acid bromide, etc.; anhydrides such as benzoic anhydride, phthalic anhydride, etc.; active esters such as benzoic acid methyl ester, benzoic acid ethyl ester, etc.; N-ethoxycarbonylphthalimide, and the like. The acylation reaction can be carried out, in general, at temperatures of 0° C. to 80° C. depending upon which of the above reactive derivatives is used.

And the reaction between a compound of the above formula (IV) and a compound of the above formula (V) can be carried out at temperatures of 0° C. to 100° C., preferably in the presence of an acid-binding agent, e.g., inorganic base such as sodium hydroxide, potassium hydroxide, potassium carbonate, etc.; or organic base such as triethylamine, diethylaniline, pyridine, etc.

The resultant compounds of formula (I) can be separated from a reaction mixture and purified by method known per se, e.g., by organic solvent extraction, silica gel or ion exchange resin column chromatography, etc.

The compounds of formula (I) provided by this invention have strong dipeptidase-inhibiting activity, and the activity can be demonstrated by the following in vitro and in vivo tests.

A. IN VITRO TEST ON DIPEPTIDASE-INHIBITING ACTIVITY

(1) Purification of Dipeptidase

Rats were sacrificed by decapitation to bleed, and about 12 g of fresh kidneys were collected. And a microsome fraction was obtained by subcellular fractionating method according to fractional centrifugation of Hogboom (Methods in Enzymology, vol. 1, pages 16-19, Academic Press, New York, 1955). This microsome fraction was treated with 400 μg/ml of trypsin at 0° C. for 16 hours, and then subjected to fractional ultracentrifugation at $10^5 G$ at 0° C. for 60 minutes.

The resultant precipitate was solubilized by 20 ml of Tris-HCl buffer (20 mM, pH 7.6) containing a surfactant (0.4% Triton ® X-100), and subjected to fractional ultracentrifugation at $10^5 G$ at 0° C. for 60 minutes. The resultant supernatant was charged to a DEAE Sephadex A-50 (Cl-model) column (15×100 mm), and then gradient elution by Tris-HCl buffer (20 mM, pH 7.6) containing a surfactant (0.4% Triton ® X-100) was carried out with salt concentrations of 0 to 0.5M.

The active fraction was concentrated with polyethylene glycol 4000, and then purified with the Tris-HCl buffer as above by using a column of Sephadex G-150 (25×900 mm) and again by using a column of Sephadex G-200 (25×900 mm) to obtain a partially purified sample of dipeptidase.

(2) Measurement of Inhibiting Activity

The enzyme obtained above (50 ml) was preincubated together with 30 μl of an inhibiting agent solution in a cuvette at 37° C. for 5 minutes. And then 0.1 ml of Tris-HCl (0.1M, pH 8.0) solution of an antibiotic PS-5 (1 mg/ml) prewarmed at 37° C. was added as a substrate to start the reaction. The reaction was carried out within a cuvette of HITACHI spectrophotometer equipped with a constant temperature device (37° C.), and decreases of absorbance at a wavelength of 301 nm for 5 minutes were determined by a recorder.

By the values obtained above and values from control containing no inhibiting agent, the percent inhibition and $ID_{50}$ at a predetermined inhibition concentration were determined. The results are shown in Table 1.

TABLE 1

| Dipeptidase-inhibiting agent | $ID_{50}$ (mM) |
| --- | --- |
| Compound No. 1 | 0.21 |
| Compound No. 2 | 0.48 |

B. IN VIVO TEST ON DIPEPTIDASE-INHIBITING ACTIVITY

Five weeks aged ddY mice were grouped five mice for one group, and aqueous solutions containing 80 or 250 mg/ml concentration of the dipeptidase-inhibiting agent of this invention (adjusted with 1N NaOH to pH 7.5) were intravenously administered to the mice. A control group was administered with a same amount of pure water. 3 to 5 minutes after the administration, 0.25 ml of an antibiotic 88617 (M/100 PBS, pH 7.0 solutions) at 5 or 20 mg/kg-mouse were subcutaneously administered to the mice.

Six hours after the administration of the antibiotic 88617, all the urines of the mice were collected and the concentrations of the antibiotic 88617 in all the collected urines were measured by disc-agar diffusion method in which *Comamonas terrigena* was used as test bacteria, and average values of five mice were determined. The results are shown in Table 2.

TABLE 2

| Recovery ratio of antibiotic 88617 in urine when dipeptidase-inhibiting agent was co-administered | |
| --- | --- |
| | Dose of antibiotic 88617 |
| Control (administration of antibiotic 88617 alone) | 20 mg/kg |
| | 27.5 (%) |
| Compound No. 1 50 mg/kg administered in combination | 38.0 |
| 250 mg/kg administered | 57.2 |

TABLE 2-continued

Recovery ratio of antibiotic 88617 in urine when dipeptidase-inhibiting agent was co-administered

| | Dose of antibiotic 88617 |
|---|---|
| in combination | |
| Antibiotic 88617 | |

[Structure of Antibiotic 88617 shown: β-lactam with F-CH(CH3)- substituent, S-CH2-C(=N-CH3)-N(CH3)2 side chain, COOH]

[See U.S. Pat. No. 4,720,490 (Japanese Laid-Open Patent Publication No. 84886/1984).]

As is clear from the results of the above tests A and B, the compounds of formula (I) have excellent inhibition activity against dipeptidase in living animals, and they are considered to be useful in administration thereof in combination with a carbapenem-type antibiotic in order to prevent metabolism of the carbapenem-type antibiotic in living animals, particularly in the kidney.

Examples of the carbapenem-type antibiotics to be effectively used in combination with the compounds of formula (I) of this invention include antibiotics PS-5, PS-6 and PS-7, thienamycin, formimidoylthienamycin, epithienamycin, carpetimycin, asparenomycin, olivanic acid, SF2103A, antibiotic 88617 and derivatives thereof.

The compounds of formula (I) of this invention may be administered orally or parenterally (e.g., intramuscularly, intravenously, or intrarectally) in the form of mixed preparations with the above carbabenem-type antibiotics or separate preparations therefrom. The range of possible dose thereof is usually 0.1 to 5 g/kg/day, preferably 100 to 1,000 mg/kg/day.

The preparation forms of the compounds of this invention may be solid forms such as tablet, capsule, dragee, suppository, etc., or liquid forms such as emulsion, etc. These preparations may be formed according to customary manner by using pharmaceutically acceptable carriers or diluents suitable for oral or parenteral administration such as water, gelatin, lactose, starch, magnesium stearate, talc vegetable oil, gum arabic, polyalkylene glycol, yellow vaseline, etc.

The following Examples will illustrate a process of preparing the compounds of formula (I) of this invention.

EXAMPLE 1

Preparation of N-benzoyl-S-(2-benzoylaminoethyl)-L-cysteine (Compound No. 1)

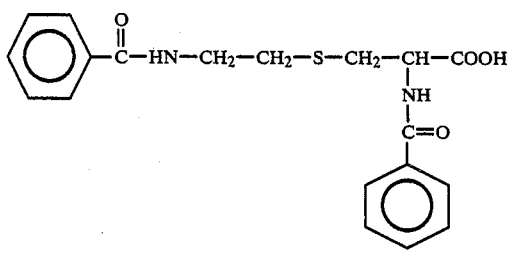

S-(2-aminoethyl)-L-cysteine dihydrochloride (1 g, 5 mmoles) was dissolved in a mixture of 5 ml of dioxane and 5 ml of water, and then cooled with ice. 1.44 ml (12.5 mmoles) of benzoyl chloride dissolved in dioxane was gradually added thereto dropwise with stirring while it was maintained at pH 9–10 with 1N sodium hydroxide. Without changing the temperature, the mixture was stirred for 2 hours, and then, after the negativity of the ninhydrin reaction in the reaction liquid was found, the reaction was stopped. The reaction liquid was extracted with the same volume of ethyl acetate. The aqueous layer was adjusted to pH 2.0 with 1N hydrochloride, and then the aqueous layer was extracted twice with the same amount of ethyl acetate. The resultant ethyl acetate layers were combined, dehydrated with anhydrous sodium sulfate and then condensed under reduced pressure. The condensate was dissolved in chloroform for crystallization. The subject compound was quantitatively obtained as white crystals.

$[\alpha]_D^{23}$ −34.5° (c 1.0, methanol)

NMR(CDCl$_3$, TMS): δ: 2.78 (2H, t, J=6.0 Hz, S—CH$_2$—CH$_2$), 3.13 (2H, m, S—CH$_2$—CH), 3.59 (2H, t, J=7.0 Hz, N—CH$_2$—CH$_2$—S), 4.97 (1H, m, S—CH$_2$—CH), 7.10–8.10 (12H, m, NH×2, Ar·H), 10.96 (1H, s, COOH).

$\gamma_{max}^{CHCl_3}$ cm$^{-1}$: 1720 (carboxylic acid), 1650 (amide).

EXAMPLE 2

Preparation of S-(2-phthalimidethyl)-N-phthaloyl-L-cysteine (Compound No. 2)

[Structure: phthalimide-N-CH2-CH2-S-CH2-CH(COOH)-N(phthaloyl)]

S-(2-aminoethyl)-L-cysteine dihydrochloride (500 mg, 2.49 mmoles) was dissolved in 10 ml of water, and 636 mg (6 mmoles) of sodium carbonate was added thereto. Then, 1.67 g (7.6 mmoles) of N-ethoxycarbonylphthalimide was gradually added to carry out the reaction. The reaction liquid was extracted twice with 20 ml of methylene chloride. Then the aqueous layer was adjusted to pH 2.0, and extracted three times with methylene chloride in a volume of 50 ml each. The extracts were combined, washed with water five times (50 ml each) and dried over Na$_2$SO$_4$. After filtration, the liquid condensed under reduced pressure was adsorbed into a silica gel column (50 ml) and the eluted with tolueneethyl acetate (1:1) and with ethyl acetate. Fractions exhibiting urtaviolet absorption at Rf value of 0.59 on a silica gel thin layer plate using ethylacetate-methanol (1:1) as an eluent were collected and evaporated under reduced pressure to give 644 mg of the subject compound as a white powder (yield 64%).

$[\alpha]_D^{23}$ −97° (c 1.0, methanol).

$\lambda_{max}^{MeOH}$ nm(ε): 293 (4400), 240 (sh) (22700).

$\gamma_{max}^{CHCl_3}$ cm$^{-1}$: 1770 (phthaloyl), 1710 (carboxylic acid).

NMR (CDCl₃, TMS): δ: 2.80 (2H, dd, J=6.0 Hz, J=7.5 Hz, S—CH₂—CH₂), 3.42 (2H, m, S—CH₂—CH), 3.81 (2H, t, J=7.0 Hz, S—CH₂—CH₂—N), 4.98 (1H, dd, J=5.0 Hz, J=10.0 Hz, S—CH₂—CH), 7.59 (8H, m, Ar·H), 8.08 (1H, s, COOH).

The following are Preparation Examples showing pharmaceutical preparations of the compounds of this invention and carbapenem antibiotics.

EXAMPLE A (Capsule)

| Ingredient | Per capsule |
|---|---|
| Antibiotic PS-5 Na salt | 100 mg |
| Compound No. 1 | 200 mg |
| Lactose (Japanese Pharmacopoeia) | suitable amount |
| Magnesium stearate | 1 mg |

The above antibiotic and excipients were milled and mixed uniformly in a mortar. No. 3 hard gelatin capsules having enteric coatings were filled with the mixture in an amount of 200 mg per capsule.

EXAMPLE B (Tablet)

| Ingredient | Per tablet |
|---|---|
| Antibiotic 88617 | 200 mg |
| Compound No. 1 | 500 mg |
| Lactose (Japanese Pharmacopoeia) | 120 mg |
| Corn starch | 175 mg |
| Magnesium stearate | 5 mg |

The antibiotic in the above amount was well mixed with corn starch in half the above amount. The mixture was mixed with 10% starch paste liquid to form particles, and the particles were sieved. The remaining corn starch and magnesium stearate were well incorporated thereto and formed into tablets having diameters of 1 cm and weights of 500 mg. The tablets were sugar-coated and then further coated with an enteric coating.

EXAMPLE C (Injectable agent)

| Ingredient | Per vial |
|---|---|
| Antibiotic 88617 | 25 mg |
| Compound No. 1 | 25 mg |

The above ingredients were dissolved in sterilized water for injection, and the solution was filtered and sterilized. The solution was poured into sterilized ampoules, the water contents were sterilely removed by freeze-drying, and the mouthes of the ampoules were closed. When used, the ampoule is opened, and 2 ml of sterilized physiological saline is added to the content of the ampoule to dissolve it.

What we claim is:

1. Compounds represented by formula

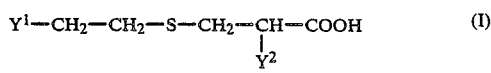

wherein $Y^1$ and $Y^2$ are identical or different, and respectively denote benzoylamino groups or phthalimide groups.

2. Compound represented by formula

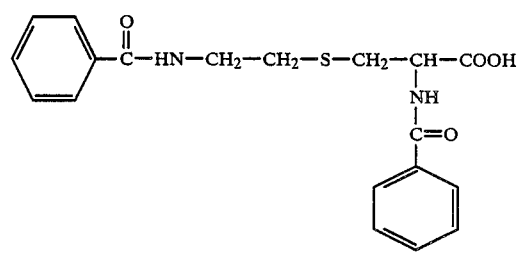

3. Compound represented by formula

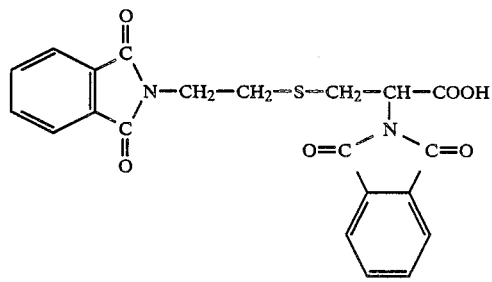

4. A pharmaceutical composition comprising a dipeptidase-inhibiting amount of a compound of the formula (I) given in claim 1 and a pharmaceutically acceptable carrier or diluent.

5. A method for inhibiting dipeptidase in a mammal which comprises administering a dipeptidase-inhibiting amount of a compound of the formula (I) given in claim 1 to the mammal.

* * * * *